(12) United States Patent
Fey

(10) Patent No.: US 6,235,908 B1
(45) Date of Patent: May 22, 2001

(54) METHOD FOR PRODUCING (S,S)-BENZYL-2,8-DIAZABICYCLO[4.3.0]NONANE

(75) Inventor: Peter Fey, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/700,107

(22) PCT Filed: Apr. 28, 1999

(86) PCT No.: PCT/EP99/02860

§ 371 Date: Nov. 9, 2000

§ 102(e) Date: Nov. 9, 2000

(87) PCT Pub. No.: WO99/58532

PCT Pub. Date: Nov. 18, 1999

(30) Foreign Application Priority Data

May 11, 1998 (DE) ............................................. 198 21 039

(51) Int. Cl.$^7$ ................................................... C07D 471/04
(52) U.S. Cl. ............................................................. 546/113
(58) Field of Search ............................................... 546/113

(56) References Cited

U.S. PATENT DOCUMENTS

| 5,480,879 | | 1/1996 | Petersen et al. | 514/202 |
| 5,654,318 | * | 8/1997 | Takemura et al. | 514/314 |
| 5,686,614 | | 11/1997 | Jones et al. | 546/43 |
| 5,723,668 | | 3/1998 | Buschmann et al. | 564/304 |

FOREIGN PATENT DOCUMENTS

| 4234330 | 4/1994 | (DE) | C07D/519/00 |
| 0550903 | 7/1993 | (EP) | C07D/471/04 |
| 0591808 | 4/1994 | (EP) | C07D/519/00 |
| 0409044 | 1/1995 | (EP) | C07D/295/08 |
| 0787715 | 8/1997 | (EP) | C07C/213/10 |
| 354975 | 8/1931 | (GB) . | |
| 9213858 | 8/1992 | (WO) | C07D/471/04 |

* cited by examiner

Primary Examiner—Bernard Dentz
(74) Attorney, Agent, or Firm—Jerry L. Chiu

(57) ABSTRACT

The invention relates to a process for preparing (S,S)-8-benzyl-2,8-diazabicyclo[4.3.0]nonane.

20 Claims, No Drawings

METHOD FOR PRODUCING (S,S)-BENZYL-2,8-DIAZABICYCLO[4.3.0]NONANE

The present invention relates to a process for preparing (S,S)-8-benzyl-2,8-diazabicyclo[4.3.0]nonane [(S,S)-benzylpyrrolopiperidine] of the formula

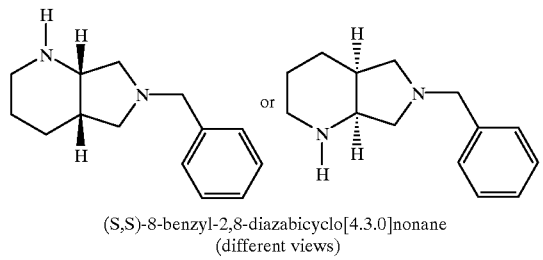

(S,S)-8-benzyl-2,8-diazabicyclo[4.3.0]nonane
(different views)

hereinbelow also referred to as (S,S)-benzylpyrrolopiperidine, by separation of the enantiomers of a mixture of (S,S)-8-benzyl-2,8-diazabicyclo[4.3.0]nonane and (R,R)-8-benzyl-2,8-diazabicyclo[4.3.0]nonane. (S,S)-8-Benzyl-2,8-diazabicyclo[4.3.0]-nonane is a useful intermediate for preparing (S,S)-2,8-diazabicyclo[4.3.0]nonane:

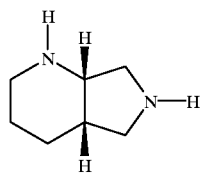

which for its part is used for preparing the antibiotic moxifloxacin (INN):

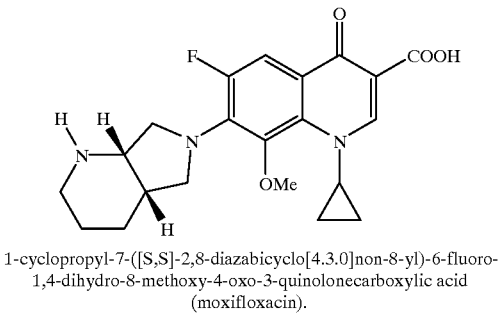

1-cyclopropyl-7-([S,S]-2,8-diazabicyclo[4.3.0]non-8-yl)-6-fluoro-1,4-dihydro-8-methoxy-4-oxo-3-quinolonecarboxylic acid
(moxifloxacin).

The preparation of racemic cis-(S,S/R,R)-8-benzyl-2,8-diazabicyclo[4.3.0]nonane is described in EP-A-0 350 733.

EP-A-0 550 903 describes various processes for the separation of the enantiomers of racemic cis-(S,S/R,R)-8-benzyl-2,8-diazabicyclo[4.3.0]nonane using D-(−)- or L-(+)-tartaric acid (Example A). These processes are carried out in dimethylformamide (DMF) as the solvent in which the racemate is dissolved. Thus, for example, according to method V (R,R)-benzylpyrrolopiperidine L-tartrate precipitates out after addition of a solution of 0.5 equivalents of L-(+)-tartaric acid in DMF to a solution of an equivalent of the cis-8-benzyl-2,8-diazabicyclo[4.3.0]nonane racemate in DMF. In a second step, the desired (S,S)-benzylpyrrolopiperidine L-(+)-tartrate is precipitated out by further addition of 0.5 equivalents of L-(+)-tartaric acid and is subsequently crystallized in pure form from ethanol/water. The tartrate is finally converted into the free amine using bases. However, this process has disadvantages with respect to the present object, since it requires prior removal of the undesired R,R enantiomer, i.e. an additional operation. Method I of Example A of EP-A-0 550 903 describes a process for the separation of the enantiomers of racemic cis-(S,S/R,R)-8-benzyl-2,8-diazabicyclo[4.3.0]nonane using D-(−)-tartaric acid in DMF. Here, the S,S-enantiomer is precipitated out first, but application of this process on an industrial scale can be ruled out owing to the high cost of the unnatural D-(−)-tartaric acid.

The solvent DMF used in the processes of EP-A-0 550 903 for the separation of the enantiomers, however, has various disadvantages. According to Römpp Lexikon Chemie Version 1.3, Stuttgart/New York: Georg Thieme Verlag 1997, entry "Dimethylformamid", DMF is readily bioabsorbed through the skin, is highly irritant to skin and mucous membranes and may damage liver and kidneys. The MAK value (maximum workplace concentration) is therefore only 10 ppm, a fact which requires special protective measures which lead to increased production costs. It was therefore desirable to develop a process for preparing (S,S)-8-benzyl-2,8-diazabicyclo-[4.3.0]nonane in which the use of problematic solvents is avoided. Furthermore, such a process should afford very high yields to avoid loss of substance, and should have few steps.

Owing to intensive investigations, the inventor surprisingly succeeded in developing a novel process for preparing (S,S)-benzylpyrrolopiperidine which permits the separation of the enantiomers of a mixture of (S,S)-8-benzyl-2,8-diazabicyclo[4.3.0]nonane and (R,R)-8-benzyl-2,8-diazabicyclo[4.3.0]nonane in high yields in unobjectionable solvents.

The invention accordingly provides a process for preparing (S,S)-8-benzyl-2,8-diaza-bicyclo[4.3.0]nonane which encompasses the reaction of a mixture of (S,S)-8-benzyl-2,8-diazabicyclo[4.3 .0]nonane and (R,R)-8-benzyl-2,8-diazabicyclo[4.3.0]nonane with L-(+)-tartaric acid in an alcohol/water mixture:

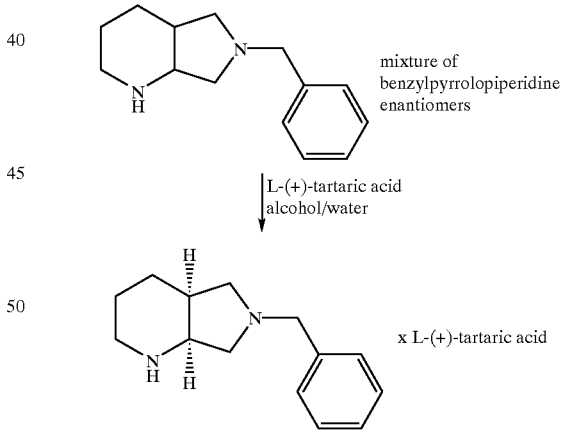

The mixture of (S,S)-8-benzyl-2,8-diazabicyclo[4.3.0]nonane and (R,R)-8-benzyl-2,8-diazabicyclo[4.3.0]nonane used according to the invention encompasses any mixtures of the S,S and R,R enantiomer. The ratio of S,S to R,R isomer is preferably from 99:1 to 40:60, particularly preferably from 99:1 to 50:50 and very particularly preferably from 99:1 to 60:40 (based on the molar amounts).

The alcohol/water solvent mixture, in which the formation of (S,S)-8-benzyl-2,8-diazabicyclo[4.3.0]nonane L-(+)-tartrate is carried out and which is used in the process of the invention, is advantageously a solvent mixture which contains at least 40% by volume, preferably at least 50% by volume, of a mixture of at least one alcohol and water, based on the total volume of the solvent used.

The alcohol/water solvent mixture used in accordance with the invention may, in addition to alcohol and water, comprise other solvents in an amount of up to 60% by volume, preferably up to 50% by volume.

The ratio by volume of alcohol to water is advantageously in a range of from 4:1 to 20:1, preferably in a ratio by volume of about 5 (alcohol) to 1 (water).

The alcohols used according to the invention in the solvent mixture are preferably one or more aliphatic, straight-chain or branched, primary, secondary or tertiary ($C_2$–$C_8$)-alcohols. These are selected, for example, from the group consisting of ethanol, n-propanol, isopropanol, n-butanol, sec-butanol, isobutanol, isoamyl alcohol and octanol. Preference is given to using n-, sec- or iso-butanol and ethanol. Very particular preference is given to n-butanol, iso-butanol and ethanol.

Solvents which may be present as further solvents in addition to alcohol and water in the alcohol/water solvent mixture used in accordance with the invention in an amount of up to 60% by volume (based on the total amount of solvent), preferably of up to 50% by volume, are selected, for example, from the group consisting of toluene, xylene, cyclohexane, ethyl acetate, methyl tert-butyl ether, etc., and preference is given to toluene. With a view to one of the objects of the present invention described above, substantial amounts of ecologically objectionable solvents, such as, for example, DMF, should be excluded, and they are preferably not present.

If the ratio of S,S to R,R isomer in the mixture of (S,S)-8-benzyl-2,8-diazabicyclo-[4.3.0]nonane and (R,R)-8-benzyl-2,8-diazabicyclo[4.3.0]nonane used according to the invention is from 99:1 to 60:40 (based on the molar amounts), preference is given to using the alcohol ethanol. Particular preference is given to an alcohol/water solvent mixture which contains only ethanol and water, advantageously by volume of from 75:25 to 95:5, preferably from 80:20 to 85:15.

If the ratio of S,S to R,R isomer in the mixture of (S,S)-8-benzyl-2,8-diazabicyclo-[4.3.0]nonane and (R,R)-8-benzyl-2,8-diazabicyclo[4.3.0]nonane used according to the invention is approximately 50:50 (based on the molar amounts), i.e. the virtually racemic mixture is used, preference is given to using the alcohol butanol. Particular preference is given to an alcohol/water solvent mixture comprising butanol (n-butanol, sec-butanol or iso-butanol) and water, advantageously in a ratio by volume of butanol:water of from 4:1 to 20:1, preferably in a ratio by volume of approximately 5:1, optionally with addition of up to 60% by volume of toluene. Very particular preference is given to an alcohol/water solvent mixture which comprises only butanol (n-butanol, sec-butanol or iso-butanol) and water, advantageously in a ratio by volume of butanol:water of from 4:1 to 20:1, preferably in a ratio by volume of approximately 5 to 1. In a further preferred embodiment of the invention, the mixture of (S,S)-8-benzyl-2,8-diazabicyclo[4.3.0]nonane and (R,R)-8-benzyl-2,8-diazabicyclo[4.3.0]nonane used according to the invention which has a ratio of S,S to R,R isomer of approximately 50:50 (based on the molar amounts) can be reacted in a solvent mixture comprising ethanol, toluene and water, the solvent mixture containing at least 40% by volume and at most 60% by volume of toluene.

For the preparation of tartrate, the solvent volumes are advantageously in the range of 2–8 litres of the alcohol/water solvent mixture used according to the invention, based on 1 kg of the mixture of (S,S)-8-benzyl-2,8-diazabicyclo[4.3.0]nonane and (R,R)-8-benzyl-2,8-diazabicyclo[4.3.0]nonane, preferably at from 2 to 4 litres, particularly preferably at approximately 3 litres per 1 kg of the mixture of (S,S)-8-benzyl-2,8-diazabicyclo[4.3.0]nonane and (R,R)-8-benzyl-2,8-diazabicyclo[4.3.0]-nonane.

In general, if racemic benzylpyrrolopiperidine is used as starting material, the L-(+)-tartaric acid is advantageously used in an amount of from 0.4 equivalents to 1 equivalent, preferably from 0.7 to 0.85 equivalents, based on 1 equivalent of the racemic benzylpyrrolopiperidine.

If a mixture of (S,S)-8-benzyl-2,8-diazabicyclo[4.3.0]nonane and (R,R)-8-benzyl-2,8-diazabicyclo[4.3.0]nonane is used in a molar ratio of from 99:1 to 60:40, and preferably if the alcohol used is ethanol, L-(+)-tartaric acid is advantageously used in an amount of from 0.8 equivalents to 1 equivalent, preferably from 0.9 to 1 equivalent, based on 1 equivalent of the mixture of (S,S)-8-benzyl-2,8-diazabicyclo[4.3.0]nonane and (R,R)-8-benzyl-2,8-diazabicyclo[4.3.0]nonane.

In a preferred embodiment of the invention, the mixture of (S,S)-8-benzyl-2,8-diazabicyclo[4.3.0]nonane and (R,R)-8-benzyl-2,8-diazabicyclo[4.3.0]nonane is dissolved in the alcohol and a solution of the L-(+)-tartaric acid in water is added. Optionally, the mixture of (S,S)-8-benzyl-2,8-diazabicyclo[4.3.0]nonane and (R,R)-8-benzyl-2,8-diazabicyclo[4.3.0]nonane can also be dissolved in a mixture of the alcohol and the other solvent, and a solution of the L-(+)-tartaric acid in water can then be added. It is also possible to choose other dosage forms for carrying out the process according to the invention, for example the addition of solid L-(+)-tartaric acid to a solution of the mixture of enantiomers in the alcohol/water solvent mixture, or the admixing of a solution of the mixture of enantiomers in an alcohol/water solvent mixture and a solution of the L-(+)-tartaric acid in an alcohol/water solvent mixture.

In the case of the preparation of tartrate, the reaction temperatures are, depending on the choice of the alcohol/water solvent mixture, in a range of from 20° C. to 110° C., preferably from 45° C. to 100° C.

The reaction time is advantageously between 1 minute and 1 hour, preferably between 5 minutes and 20 minutes.

After the reaction of the mixture of (S,S)-8-benzyl-2,8-diazabicyclo[4.3.0]nonane and (R,R)-8-benzyl-2,8-diazabicyclo[4.3.0]nonane with the L-(+)-tartaric acid, preference is given to seeding with (S,S)-benzylpyrrolopiperidine L-(+)-tartrate, preferably in a temperature range of from 20° C. to 110° C., particularly preferably at from 40° C. to 60° C. Under these conditions, crystallization of the (S,S)-8-benzyl-2,8-diazabicyclo[4.3.0]nonane L-(+)-tartrate does already take place. To complete the crystallization, stirring of the mixture is continued, depending on the given solvent mixture and the concentration of the tartrate formed, advantageously in a temperature range of from 0 to 30° C., preferably at room temperature (25° C.).

In a further embodiment, the (S,S)-8-benzyl-2,8-diazabicyclo[4.3.0]nonane L-(+)-tartrate prepared in the reaction of the mixture of (S,S)-8-benzyl-2,8-diazabicyclo-[4.3.0]nonane and (R,R)-8-benzyl-2,8-diazabicyclo[4.3.0]nonane with L-(+)-tartaric acid can be purified further by recrystallization from an alcohol/water mixture. Here, the alcohol is preferably at least an aliphatic alcohol which is particularly preferably chosen from the group consisting of n-, sec-, iso-butanol and ethanol.

The ratio by volume of alcohol to water for the recrystallization is preferably in a range of from 95:5 to 80:20.

The ratio by volume of alcohol to water for the recrystallization is for ethanol preferably in a range of from 95:5 to 80:20, particularly preferably at approximately 85 to 15, and for butanol preferably in a range of from 4:1 to 20:1, particularly preferably in a range of from 5:1 to 10:1.

The solvent volumes for the recrystallization are advantageously in the range of approximately 2 to 12 litres, preferably 2.5 to 11, particularly preferably 4 to 9 litres of alcohol/water, for ethanol preferably from 2.5 to 11 litres of ethanol/water and for butanol preferably 7–12 litres of butanol/water, in each case per 1 kg of (S,S)-8-benzyl-2,8-diazabicyclo[4.3.0]nonane L-(+)-tartrate. Particular preference is given to 4–6 litres of ethanol/water or 8–9 litres of butanol/water per 1 kg of (S,S)-8-benzyl-2,8-diazabicyclo[4.3.0]nonane L-(+)-tartrate.

The temperatures for the dissolution process in the recrystallization are, depending on the choice of the mixture of alcohol/water, in a range of from 70° C. to 120° C., preferably at from 78° C. to 100° C.

In a preferred embodiment, during the recrystallization, seeding is carried out with (S,S)-8-benzyl-2,8-diazabicyclo[4.3.0]nonane L-(+)-tartrate, advantageously in a temperature range of from 70° C. to 120° C., preferably at from 80° C. to 90° C.

The (S,S)-8-benzyl-2,8-diazabicyclo[4.3.0]nonane L-(+)-tartrate obtained in the reaction carried out according to the invention is, if appropriate after recrystallization, converted in a manner known per se into the free (S,S)-8-benzyl-2,8-diazabicyclo[4.3.0]nonane by reaction with base(s) (see, for example, EP-A-0550903, Example A, Method 1). This can then be used to obtain, for example by hydrogenation in a manner known per se, (S,S)-2,8-diazabicyclo[4.3.0]nonane (see, for example, EP-A-0 350 733, Example K).

EXAMPLE 1

(S,S)-Benzylpyrrolopiperidine tartrate

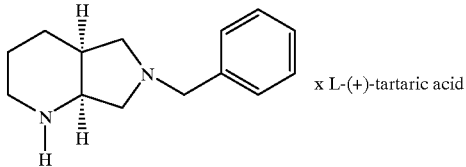

10 g (46.2 mmol) of benzylpyrrolopiperidine are dissolved in 25 ml of 1-butanol and heated to 100° C. A solution of 5.5 g (37 mmol) of L-(+)-tartaric acid in 5 ml of water is added, and the mixture is stirred at 100° C. for 5 min. Heating is removed and the solution is, at 48° C., seeded with (S,S)-benzylpyrrolopiperidine tartrate and stirred at room temperature overnight. The precipitated crystals are filtered off with suction, washed with a little butanol and dried in a vacuum drying cabinet at 45° C. to give 8.6 g of (S,S)-benzylpyrrolopiperidine tartrate (hydrate), 95.7% ee (ee=enantiomeric excess).

Drying at 80° C. over phosphorus pentoxide gives 7.6 g of (S,S)-benzyl-pyrrolopiperidine tartrate.

Yield: 44.9%

EXAMPLE 2

(S,S)-Benzylpyrrolopiperidine tartrate

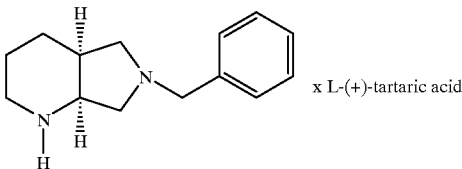

100 g (462 mmol) of benzylpyrrolopiperidine are dissolved in 250 ml of 1-butanol. At room temperature, a solution of 55 g (370 mmol) of L-(+)-tartaric acid in 50 ml of water is added, and during the addition the solution warms to about 46° C. The solution is seeded with (S,S)-benzylpyrrolopiperidine tartrate and stirred at room temperature overnight. The precipitated crystals are filtered off with suction, washed with 50 ml of butanol/water 5:1 and dried in a vacuum drying cabinet at 45° C. to give 82.9 g of (S,S)-benzylpyrrolopiperidine tartrate (hydrate), 94.3% ee.

Drying at 80° C. over phosphorus pentoxide gives 76.2 g of (S,S)-benzyl-pyrrolopiperidine tartrate.

Yield: 43.8%

EXAMPLE 3

By the method of Example 1, experiments were carried out in the solvents below, by adding the L-(+)-tartaric acid, dissolved in water, to a solution of the racemic benzylpyrrolopiperidine in the organic solvents:

| Solvent mixture (ratio by volume) | Yield (% of theory) | Enantiomeric excess |
| --- | --- | --- |
| sec-butanol/water (5:1) | 43.7% | 92.4% ee SS |
| i-butanol/water (5:1) | 44.9% | 96.0% ee SS |
| isoamyl alcohol/water (5:1) | 35.5% | 95.4% ee SS |
| octanol/water (5:1) | 41.1% | 89.9% ee SS |
| butanol/toluene/water (5:5:1) | 41.1% | 94.3% ee SS |
| toluene/ethanol/water (5:5:1) | 36.9% | 93.2% ee SS |

EXAMPLE 4

(S,S)-Benzylpyrrolopiperidine tartrate

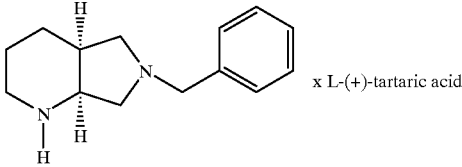

8 g (37.0 mmol) of (S,S)-benzylpyrrolopiperidine, 2 g (9.2 mmol) of (R,R)-benzyl-pyrrolopiperidine and 6.2 g (41.3 mmol) of L-(+)-tartaric acid are dissolved in 88 ml of ethanol/water (85:15/vol./vol.) and heated to reflux temperature (about 78° C.). The mixture is stirred at this temperature for 5 min, heating is removed, the solution is seeded at about 45° C. with (S,S)-benzylpyrrolopiperidine L-(+)-tartrate and stirred at room temperature overnight. The precipitated crystals are filtered off with suction, washed with 15 ml of ethanol and dried in a vacuum drying cabinet at 75° C. to give 12.9 g of (S,S)-benzylpyrrolopiperidine tartrate 98.2% ee (ee=enantiomeric excess).

Yield: 94.4% based on the (S,S)-benzylpyrrolopiperidine used

EXAMPLE 5
(S,S)-Benzylpyrrolopiperidine tartrate

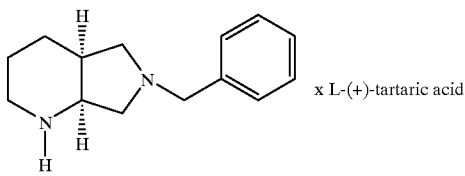 x L-(+)-tartaric acid 6 g (27.8 mmol) of (S,S)-benzylpyrrolopiperidine, 4 g (18.4 mmol) of (R,R)-benzyl-pyrrolopiperidine and 5.5 g (36.6 mmol) of L-(+)-tartaric acid are dissolved in 88 ml of ethanol/water (85:15/vol./vol.) and heated to reflux temperature (about 78° C.).

The mixture is stirred at this temperature for 5 min, heating is removed, the solution is seeded at about 45° C. with (S,S)-benzylpyrrolopiperidine L-(+)-tartrate and stirred at room temperature overnight. The precipitated crystals are filtered off with suction, washed with 15 ml of ethanol and dried in a vacuum drying cabinet at 75° C. to give 10.0 g of (S,S)-benzylpyrrolopiperidine tartrate 96.9% ee (ee= enantiomeric excess).

Yield: 98.1% based on the (S,S)-benzylpyrrolopiperidine used

EXAMPLE 6
(S,S)-Benzylpyrrolopiperidine tartrate (recrystallization)

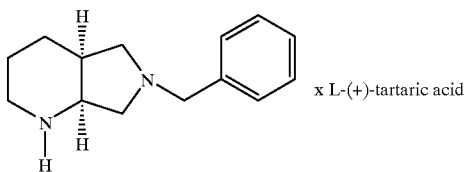 x L-(+)-tartaric acid 10 g of the crystals from Example 1 were dissolved in 80 ml of 1-butanol/water (10:1/vol./vol.) at boiling point. The heating bath was removed and the solution was seeded at about 88° C. and stirred at room temperature overnight. The precipitated crystals were filtered off with suction, washed with a little butanol and dried at 45° C. under reduced pressure.

Yield: 9.9 g, 99.6% ee

EXAMPLE 7
(S,S)-Benzylpyrrolopiperidine tartrate

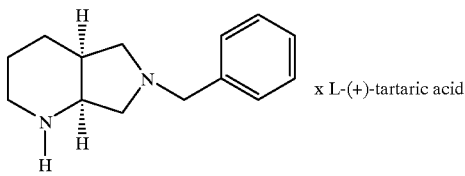 x L-(+)-tartaric acid 10 g of the crystals from Example 1 were dissolved in 52 ml of ethanol/water (85:15/vol./vol.) at boiling point. The heating bath was removed and the solution was seeded at about 55° C. and stirred at room temperature overnight. The precipitated crystals were filtered off with suction, washed with a little ethanol and dried at 45° C. under reduced pressure.

Yield: 9.9 g, 99.6% ee

EXAMPLE 8
(S,S)-Benzylpyrrolopiperidine

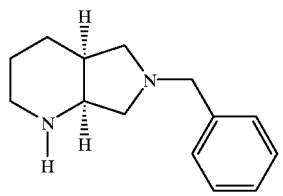

40 g of the crystals from Example 5 were dissolved in 125 ml of water, stirred with 125 ml of toluene and made alkaline using 20 ml of conc. aqueous sodium hydroxide solution. The toluene phase was separated off and concentrated under reduced pressure to give 23.0 g. The crude product was distilled under reduced pressure.

Yield: 20.8 g b.p.:104° C./0.1 mbar

What is claimed is:

1. Process for preparing (S,S)-8-benzyl-2,8-diazabicyclo[4.3.0]nonane, comprising reacting a mixture of (S,S)-8-benzyl-2,8-diazabicyclo[4.3.0]nonane and (R,R)-8-benzyl-2,8-diazabicyclo[4.3.0]nonane with L-(+)-tartaric acid in an alcohol/water solvent mixture and converting the (S,S)-8-benzyl-2,8-diazabicyclo[4.3.0]nonane L-(+)-tartrate formed by said reaction into the free (S,S)-8-benzyl-2,8-diazabicyclo[4.3.0]nonane by reacting said (S,S)-8-benzyl-2,8-diazabicyclo[4.3.0]nonane L-(+)-tartrate with a base.

2. Process according to claim 1, wherein the molar ratio in the mixture used of (S,S)-8-benzyl-2,8-diazabicyclo[4.3.0]nonane to (R,R)-8-benzyl-2,8-diazabicyclo[4.3.0]nonane is 99:1 to 40:60.

3. Process according to claim 1 wherein the molar ratio in the mixture used of (S,S)-8-benzyl-2,8-diazabicyclo[4.3.0]nonane to (R,R)-8-benzyl-2,8-diazabicyclo[4.3.0]nonane is between 99:1 and 60:40.

4. Process according to claim 1 wherein the alcohol/water solvent mixture contains at least 40% by volume, of a mixture of at least one alcohol and water, based on the total volume of the solvent used.

5. Process according to claim 1 wherein the ratio by volume of alcohol to water in the alcohol/water solvent mixture is in a range of from 4:1 to 20:1.

6. Process according to claim 1 wherein the ratio of S,S to R,R isomer in the mixture of (S,S)-8-benzyl-2,8-diazabicyclo[4.3.0]nonane and (R,R)-8-benzyl-2,8-diazabicyclo[4.3.0]nonane is in a range from 99:1 to 60:40 (based on the molar amounts), and the alcohol/water solvent mixture comprises ethanol and water.

7. Process according to claim 1 wherein the ratio of S,S to R,R isomer in the mixture of (S,S)-8-benzyl- 2,8-diazabicyclo[4.3.0]nonane and (R,R)-8-benzyl-2,8-diazabicyclo[4.3.0]nonane is approximately 50:50 (based on the molar amounts), and the alcohol/water solvent mixture comprises butanol (n-butanol, sec-butanol or iso-butanol) and water, in a ratio by volume of butanol:water of from 4:1 to 20:1.

8. Process according to claim 1, wherein from 2–8 litres of the alcohol/water solvent mixture are used, based on 1 kg. of the mixture of (S,S)-8-benzyl-2,8-diazabicyclo[4.3.0]nonane and (R,R)-8-benzyl-2,8-diazabicyclo[4.3.0]nonane.

9. Process according to claim 1 where a mixture of (S,S)-8-benzyl-2,8-diazabicyclo[4.3.0]nonane and (R,R)-8-benzyl-2,8-diazabicyclo[4.3.0]-nonane is dissolved in alcohol and a solution of the L-(+)-tartaric acid in water is added.

10. Process according to claim 1 wherein the reaction temperature is in a range of from 20° C. to 110° C.

11. Process according to claim 1 wherein, after the reaction of the mixture of (S,S)-8-benzyl-2,8-diazabicyclo[4.3.0]nonane and (R,R)-8-benzyl-2,8-diazabicyclo[4.3.0]nonane with the L-(+)-tartaric acid, seeding with (S,S)-8-benzyl-2,8-diazabicyclo[4.3.0]nonane L-(+)-tartrate is carried out.

12. Process according to claim 1 wherein the (S,S)-8-benzyl-2,8-diazabicyclo[4.3.0]nonane L-(+)-tartrate prepared in the reaction of the mixture of (S,S)-8-benzyl-2,8-diazabicyclo[4.3.0]nonane and (R,R)-8-benzyl-2,8-diazabicyclo[4.3.0]nonane with L-(+)-tartaric acid is purified further by recrystallization from an alcohol/water mixture.

13. Process for preparing (S,S)-2,8-diazabicyclo[4.3.0]nonane, characterized in that the (S,S)-8-benzyl-2,8-diazabicyclo[4.3.0]nonane obtained according to claim 1 is subjected to hydrogenolytic cleavage of the benzyl group.

14. The process of claim 6, wherein a ratio by volume of ethanol to water in said alcohol/water mixture is in a range of 75:25 to 95:5.

15. The process of claim 7, wherein a ratio by volume of butanol to water in said alcohol/water mixture is about 5:1.

16. The process of claim 7, further comprising adding up to 60% by volume of toluene.

17. The process of claim 10, wherein said reaction temperature is in a range of 45° C. to 100° C.

18. The process of claim 11, wherein said reaction temperature is in a range of 20° C. to 110° C.

19. The process of claim 18, wherein said reaction temperature is in a range of 40° C. to 50° C.

20. The process of claim 1, further comprising recrystallization of the (S,S)-8-benzyl-2,8-diazabicyclo[4.3.0]nonane L-(+)-tartrate formed prior to conversion to the free (S,S)-8-benzyl-2,8-diazabicyclo[4.3.0]nonane.

* * * * *